United States Patent
Lu et al.

(10) Patent No.: US 11,602,721 B2
(45) Date of Patent: *Mar. 14, 2023

(54) CURED BIODEGRADABLE MICROPARTICLES AND SCAFFOLDS AND METHODS OF MAKING AND USING THE SAME

(71) Applicant: THE SECANT GROUP, LLC, Telford, PA (US)

(72) Inventors: Steven Lu, Cambridge, MA (US); Peter D. Gabriele, Frisco, TX (US); Julia Donnelly, Chalfront, PA (US); Brian Ginn, Chalfont, PA (US); Charles Brendan Nicholson, Coopersburg, PA (US); Jeremy J. Harris, Doylestown, PA (US); Michael S. Flemmens, Redmond, WA (US)

(73) Assignee: THE SECANT GROUP, LLC, Telford, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/735,251

(22) Filed: Jan. 6, 2020

(65) Prior Publication Data

US 2020/0139330 A1    May 7, 2020

Related U.S. Application Data

(63) Continuation of application No. 15/941,745, filed on Mar. 30, 2018, now Pat. No. 10,556,217.

(60) Provisional application No. 62/547,559, filed on Aug. 18, 2017, provisional application No. 62/479,661, filed on Mar. 31, 2017.

(51) Int. Cl.
| | |
|---|---|
| *B01J 13/08* | (2006.01) |
| *A61L 27/56* | (2006.01) |
| *A61L 27/54* | (2006.01) |
| *A61L 27/18* | (2006.01) |
| *A61L 27/20* | (2006.01) |
| *A61L 27/26* | (2006.01) |
| *A61L 15/42* | (2006.01) |
| *A61L 15/44* | (2006.01) |
| *A61L 15/64* | (2006.01) |
| *A61L 15/22* | (2006.01) |
| *C09J 133/06* | (2006.01) |
| *C09J 123/20* | (2006.01) |
| *A61L 27/58* | (2006.01) |
| *C08J 9/24* | (2006.01) |
| *A61L 31/04* | (2006.01) |
| *A61L 27/14* | (2006.01) |
| *A61L 24/00* | (2006.01) |
| *A61L 24/04* | (2006.01) |

(52) U.S. Cl.
CPC ............... *B01J 13/08* (2013.01); *A61L 15/22* (2013.01); *A61L 15/225* (2013.01); *A61L 15/425* (2013.01); *A61L 15/44* (2013.01); *A61L 15/64* (2013.01); *A61L 24/0015* (2013.01); *A61L 24/0036* (2013.01); *A61L 24/0042* (2013.01); *A61L 24/04* (2013.01); *A61L 24/043* (2013.01); *A61L 27/14* (2013.01); *A61L 27/18* (2013.01); *A61L 27/20* (2013.01); *A61L 27/26* (2013.01); *A61L 27/54* (2013.01); *A61L 27/56* (2013.01); *A61L 27/58* (2013.01); *A61L 31/04* (2013.01); *C08J 9/24* (2013.01); *C09J 123/20* (2013.01); *C09J 133/06* (2013.01); *A61L 2300/404* (2013.01); *A61L 2300/41* (2013.01)

(58) Field of Classification Search
None
See application file for complete search history.

(56) References Cited

U.S. PATENT DOCUMENTS

| | | | |
|---|---|---|---|
| 3,487,132 | A | 12/1969 | Thorne |
| 4,632,964 | A | 12/1986 | Altschuler et al. |
| 4,664,978 | A | 5/1987 | Wu et al. |
| 4,863,974 | A | 9/1989 | Mallouk et al. |

(Continued)

FOREIGN PATENT DOCUMENTS

| | | |
|---|---|---|
| CN | 104629023 A | 5/2015 |
| EP | 0618249 A3 | 5/1994 |

(Continued)

OTHER PUBLICATIONS

Aydin et al. Biomaterials Science 2013 1:503-509 (Year: 2013).*
Snow www.thefreelibrary.com/_/print/PrintArticle.aspx?id=70434762 (Year: 2001).*
Zhang et al. Polymer Testing 2016 54:118-125 (Year: 2016).*

(Continued)

*Primary Examiner* — Melissa S Mercier
*Assistant Examiner* — Caralynne E Helm
(74) *Attorney, Agent, or Firm* — McNees Wallace & Nurick LLC

(57) ABSTRACT

A method of forming cured microparticles includes providing a poly(glycerol sebacate) resin in an uncured state. The method also includes forming the composition into a plurality of uncured microparticles and curing the uncured microparticles to form the plurality of cured microparticles. The uncured microparticles are free of a photo-induced crosslinker. A method of forming a scaffold includes providing microparticles including poly(glycerol sebacate) in a three-dimensional arrangement. The method also includes stimulating the microparticles in the three-dimensional arrangement to sinter the microparticles, thereby forming the scaffold having a plurality of pores. A scaffold is formed of a plurality of microparticles including a poly(glycerol sebacate) thermoset resin in a three-dimensional arrangement. The scaffold has a plurality of pores.

23 Claims, 9 Drawing Sheets

(56) References Cited

U.S. PATENT DOCUMENTS

| | | | |
|---|---|---|---|
| 4,891,409 A | 1/1990 | Kuan et al. | |
| 4,917,835 A | 4/1990 | Lear et al. | |
| 5,108,833 A * | 4/1992 | Noguchi | B29C 67/205 |
| | | | 181/290 |
| 6,017,566 A | 1/2000 | Bunczek et al. | |
| 6,444,782 B1 | 9/2002 | Hamlin | |
| 7,645,504 B1 | 1/2010 | Pacetti | |
| 7,722,894 B2 | 5/2010 | Wang et al. | |
| 8,716,410 B2 | 5/2014 | Venkatraman et al. | |
| 9,359,472 B2 | 6/2016 | Nicholson et al. | |
| 2003/0118692 A1 | 6/2003 | Wang et al. | |
| 2004/0039440 A1 | 2/2004 | Elmach | |
| 2004/0057985 A1 | 3/2004 | Bracht | |
| 2005/0133046 A1 | 6/2005 | Becker et al. | |
| 2005/0169958 A1 | 8/2005 | Hunter et al. | |
| 2006/0009839 A1 | 1/2006 | Tan | |
| 2007/0023974 A1 | 2/2007 | Wu | |
| 2007/0088114 A1 | 4/2007 | Asgari | |
| 2007/0281031 A1 | 12/2007 | Yang | |
| 2008/0124451 A1 | 5/2008 | Pacetti | |
| 2009/0011486 A1 | 1/2009 | Bettinger et al. | |
| 2009/0018306 A1 | 1/2009 | Rosing et al. | |
| 2009/0082840 A1 | 3/2009 | Rusk et al. | |
| 2009/0214373 A1 | 8/2009 | Stinson et al. | |
| 2009/0263359 A1 | 10/2009 | Ferreira et al. | |
| 2010/0094404 A1 | 4/2010 | Greenhalgh et al. | |
| 2010/0228358 A1 | 9/2010 | Leonard et al. | |
| 2011/0038910 A1 | 2/2011 | Faucher et al. | |
| 2011/0142790 A1 | 6/2011 | Chen | |
| 2012/0064027 A1 | 3/2012 | Shalaby | |
| 2012/0143347 A1 | 6/2012 | Wang et al. | |
| 2012/0305490 A1 | 12/2012 | Schroen et al. | |
| 2013/0147094 A1 | 6/2013 | Melamed et al. | |
| 2015/0320542 A1 | 11/2015 | Gabriele et al. | |
| 2015/0344618 A1 | 12/2015 | Nicholson et al. | |
| 2016/0038289 A1* | 2/2016 | Noble | A61L 27/34 |
| | | | 623/17.19 |
| 2016/0046832 A1 | 2/2016 | Wroblesky et al. | |
| 2016/0242895 A1 | 8/2016 | Matheny | |
| 2016/0251540 A1 | 9/2016 | Nicholson et al. | |
| 2017/0246316 A1 | 8/2017 | Wroblesky et al. | |
| 2017/0290950 A1 | 10/2017 | Wagner et al. | |
| 2018/0050128 A1 | 2/2018 | Gabriele et al. | |

FOREIGN PATENT DOCUMENTS

| | | |
|---|---|---|
| GB | 1419128 A | 12/1972 |
| JP | 03047870 A | 2/1991 |
| WO | 00/55236 A1 | 9/2000 |
| WO | 2009009749 A1 | 1/2009 |
| WO | 2009067482 A1 | 5/2009 |
| WO | 2016/57662 A1 | 4/2016 |
| WO | 2017147457 A2 | 8/2017 |
| WO | 2018/220621 A2 | 12/2018 |
| WO | 2018/220622 A2 | 12/2018 |
| WO | 2018/220623 A1 | 12/2018 |

OTHER PUBLICATIONS

Shin et al. Journal of Biomedical Materials Research Part A 2008 84A:702-709 (Year: 2008).*
Lin et al. (Journal of Microencapsulation 1999 16(5):639-646 (Year: 1999).*
Saralidze et al. Materials 2010 3:3537-3564 (Year: 2010).*
Tallawi et al. Tissue Engineering: Part C 2015 21(6):585-595 (Year: 2015).*
Frydrych et al. Polymer Chemistry 2015 6:7974-7987 and Electronic Supplementary material at www.rsc.org/suppdata/c5/py/c5py01136a/c5py01136a2.pdf?_ga=2.212513808.54351313.1633464170-395150601.1585933211 (Year: 2015).*
Mineral oil MSDS (Year: 2008).*
Borden et al. Biomaterials 2002 23:551-559 (Year: 2002).*
Sinter. Collins Dictionary HarperCollins Publishers (Year: 2014).*
Barrere et al., "Polyester synthesis in aqueous miniemulsions", Polymer, vol. 44, pp. 2833-2841, (2003).
Cataldo et al., "Biodiesel as a Plasticizer of a SBR-Based Tire Tread Formulation", ISRN Polymer Science, vol. 2013, 9 pages, (2013).
Chen et al., "Characterisation of a soft elastomer poly(glycerol sebacate) designed to match the mechanical properties of myocardial tissue", Biomaterials, vol. 29, pp. 47-57, (2008).
Curl et al., "Quantum cascade lasers in chemical physics", Chemical Physics Letters, vol. 487, pp. 1-18, (2010).
Gabriele et al., "Infrared Imaging: A Complementary Tool to AFM for Adhesive Surface Analysis", Adhesives Age, pp. 33-47 (2001).
Gao et al., "Macroporous Elastomeric Scaffolds with Extensive Micropores for Soft Tissue Engineering", Tissue Engineering, vol. 12, pp. 917-925, (2006).
Guo et al., "Characterization and optimization of glycerol/sebacate ratio in poly(glycerol-sebacate) elastomer for cell culture application", J. Biomed Mater. Res. Part A, vol. 102A, pp. 3903-3907, (2014).
Jaafar et al., "Spectroscopic evaluation, thermal, and thermomechanical characterization of poly(glycerol-sebacate) with variations in curing temperatures and durations", J. Mater. Sci., vol. 45, pp. 2525-2529, (2009).
Jain et al., "Preparation and in vitro characterization of mucoadhesive Norethisterone—egg albumin microspheres for nasal administration", Asian Journal of Biomedical & Pharmaceutical Sciences, vol. 2, pp. 49-57, (2012).
Klapper et al., "Oil-in-Oil Emulsions: A Unique Tool for the Formation of Polymer Nanoparticles", Accounts of chemical research, vol. 41, pp. 1190-1201 (2008).
Kotidis, "Quantum cascade Lasers: QCLs enable applications in IR spectroscopy", LaserFocusWorld, 6 pages, (dated Jan. 1, 2013), available at http://www.laserfocusworld.com/articles/print/volume-49/issue-01/features/quantum-cascade-lasers-qcls-enable-applications-in-ir-spectrosc.html.
Lee et al., "Substantial expression of mature elastin in arterial constructs", Proceedings of the National Academy of Sciences, vol. 108, pp. 2705-2710, (2011).
Louage et al., "Poly(glycerol sebacate) nanoparticles for encapsulation of hydrophobic anti-cancer drugs", Polymer Chemistry, vol. 8, pp. 5033-5038, (2017).
Pryor et al., "Poly(glycerol sebacate) films prevent postoperative adhesions and allow laparoscopic placement", Surgery, vol. 146, pp. 490-497, (2009).
Rai et al., "Synthesis, properties and biomedical applications of poly(glycerol sebacate) (PGS): A review", Progress in Polymer Science, vol. 37, pp. 1051-1078, (2012).
Ramesh et al., "Comparison of Oil-in-Oil, Water-in-Oil-in-Water and Melt Encapsulation Techniques for the Preparation of Controlled Release B12 Poly (eta-caprolactone) Microparticles", Trends Biomater. Artif. Organs, vol. 23, pp. 21-33, (2009).
Sun et al., "The influence of lactic acid on the properties of Poly (glycerol-sebacate-lactic acid)", Materials Science and Engineering C, vol. 29, pp. 178-182, (2009).
The Olive Oil Source, "What is the boiling point of olive oil", dated Nov. 7, 2005, available at https://www.oliveoilsource.com/asktheexpert/what-boiling-point-olive-oil, 1 page.
Wang et al. "A Tough Biodegradable Elastomer", Nature Biotechnology, vol. 20, pp. 602-606, (2002).
Wu et al., "Fabrication and characterization of monodisperse PLGA-alginate core-shell microspheres with monodisperse size and homgeneous shells for controlled drug release", Acta Biomaterialia, vol. 9, pp. 7410-7419, (2013).

* cited by examiner

CURED BIODEGRADABLE MICROPARTICLES AND SCAFFOLDS AND METHODS OF MAKING AND USING THE SAME

CROSS-REFERENCE TO RELATED APPLICATIONS

This application is a continuation application of U.S. patent application Ser. No. 15/941,745 filed Mar. 30, 2018, which claims priority to and the benefit of U.S. Provisional Application No. 62/479,661 filed Mar. 31, 2017, and U.S. Provisional Application No. 62/547,559 filed Aug. 18, 2017, all of which are hereby incorporated by reference in their entirety herein.

FIELD OF THE INVENTION

The present disclosure is generally directed to cured configurations of biodegradable polymeric elastomers.

BACKGROUND OF THE INVENTION

Poly(glycerol sebacate) (PGS) is a cross-linkable elastomer formed as a co-polymer from glycerol and sebacic acid. PGS is biocompatible and biodegradable, reduces inflammation, improves healing, and has antimicrobial properties, all of which make it useful as a biomaterial in the biomedical field.

To create a PGS thermoset/solid structure, neat PGS resin must be crosslinked/cured at elevated temperatures. However, at physiological temperatures, PGS resin is a liquid and flows, thus limiting the application of neat PGS resin. Therefore, it is generally required to cast the PGS resin in a mold to hold the PGS resin shape during the crosslinking step at an elevated temperature to create a shaped thermoset structure.

As a result, creating any kind of spherical conformations of PGS is especially difficult, even more so when microparticles or microspheres are the intended article. PGS microparticles may be created from neat PGS resin through emulsion and solvent evaporation, but subsequent thermal processing steps to cure the PGS microparticles result in melting the PGS microparticles and a loss of their spherical conformation.

Other methods of making crosslinked PGS structures involve the use of a dissolvable solid form, addition of fillers to "solidify" the resin, or changing the chemistry of PGS to allow for crosslinking methods other than thermal curing.

U.S. Pub. No. 2009/0011486 describes nano/microparticles formed from poly(glycerol sebacate acrylate) (PGSA). However, this involves incorporating photo-crosslinkers into PGSA and ultraviolet (UV)-curing the PGSA microparticles to form solid particles. UV photoinitiators and catalytic crosslink agents are known to elicit immune responses to both the toxicity and by-products of use, making such particles unfavorable for use in biological systems.

BRIEF DESCRIPTION OF THE INVENTION

What is needed is a method of particalizing PGS resin compositions and making microparticles containing PGS in a spherical conformation that can be performed without the need to use forms, thermoset fillers, or the introduction of photo-induced crosslinkers or other initiators which may be harmful in biological systems.

Lactide and glycolide microparticles are difficult to formulate and are hard and rigid limiting their use while elastomers are notoriously difficult to process into shapes without a mold. Embodiments of present invention allow for mold-free formation of an elastomeric particle that extends or provides certain properties that rigid polymers cannot provide like deformation and compressibility.

PGS microparticles can be used in the development of elastomeric, surface eroding microparticles with tunable degradation kinetics for a final article of manufacture. The PGS microparticles can be designed according to stoichiometry of starting materials, degree of crosslink or particle formation method (e.g. encapsulation, micellular, emulsion).

In an embodiment, a method of forming a plurality of cured microparticles includes providing a composition comprising a poly(glycerol sebacate) resin in an uncured state and forming the composition into a plurality of uncured microparticles, the plurality of uncured microparticles being free of a photo-induced crosslinker, and curing the plurality of uncured microparticles to form the plurality of cured microparticles.

In some embodiments, the step of forming includes combining the PGS resin composition with a phase-incompatible liquid. In some embodiments the phase-incompatible liquid is an oil; in some embodiments the phase-incompatible liquid is an elastomer; in some embodiments, the phase-incompatible liquid is capable of undergoing a reversible sol-gel transition.

In another embodiment, a method of forming a scaffold includes providing a plurality of microparticles comprising poly(glycerol sebacate) in a three-dimensional arrangement and stimulating the plurality of microparticles to sinter them into the scaffold.

In yet another embodiment, a scaffold is formed of a plurality of microparticles comprising a poly(glycerol sebacate) thermoset resin in a three-dimensional arrangement, the scaffold having a plurality of pores.

Various features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Figure 1:
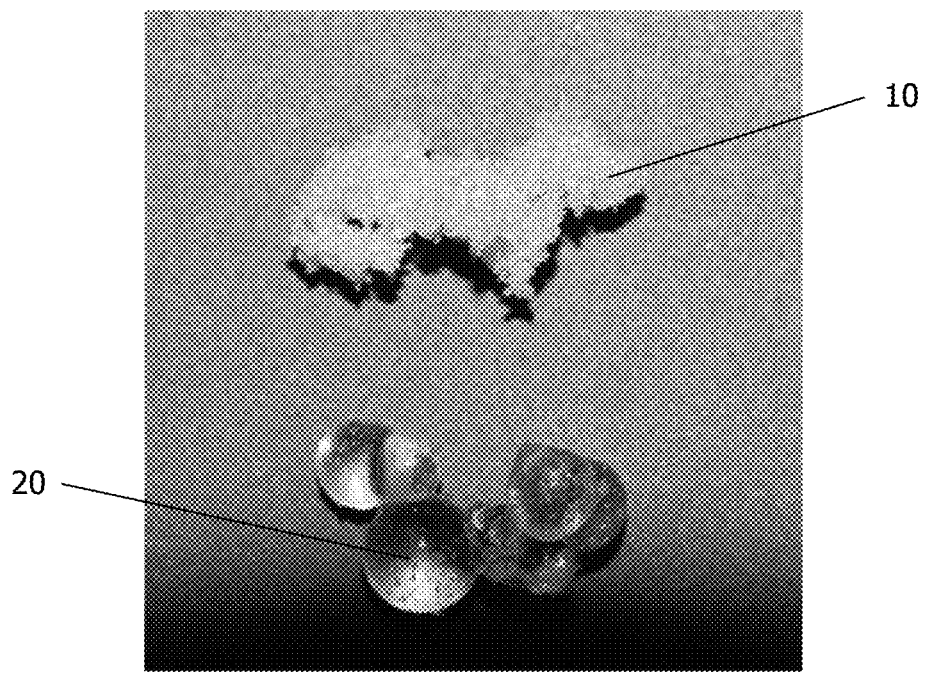
FIG. 1 is an image of different sizes of cured PGS particles in embodiments of the present disclosure.

Provided are cured biodegradable particles, scaffolds, methods of making and using cured biodegradable particles and scaffolds as well as compositions containing cured biodegradable particles.

Exemplary embodiments provide convertible microparticles that are supported without a mold during transition from an uncured to cured state.

Embodiments of the present disclosure, for example, in comparison to concepts failing to include one or more of the features disclosed herein, provide spherical poly(ol)-diacid co-polymer particles without the use of a mold, provide spherical PGS particles without the use of a mold, provide spherical PGS microparticles, provide spherical PGS nanoparticles, provide PGS microparticles free of photoinitiator, provide PGS microparticles consisting of PGS polymer, provide PGS microparticles free of any chemical component that would react with the PGS polymer during curing, provide three-dimensional (3-D) scaffolds from PGS microparticles, provide drug-loaded PGS microparticles, provide drug-coated PGS microparticles, provide cured microparticles free of photoinitiator, provide cured microparticles free of additives, provide microparticles free of photo-induced crosslinkers, permit visualization of the surface chemical structure of a pressure-sensitive adhesive, promote incorporation of an active pharmaceutical ingredient (API) into compositions for controlled release of the API, or combinations thereof.

As used herein, the term "microparticle" refers to a particle having a largest dimension between 1 micrometer (μm) and 1000 μm. The term encompasses a plurality of geometric shapes. Thus, microparticles may be either regular or irregular or of a geometrically distinct shape, such as, for example, spherical or rough. In some presently preferred embodiments, the microparticles are spherical.

As used herein, the term "nanoparticle" refers to a particle having a largest dimension between 1 nanometer (nm) and 1000 nm.

The present disclosure relates to processes of making microparticles and modulated porous microparticle-based cell scaffold technologies including poly(glycerol sebacate) (PGS), PGS microparticles formed from such processes including flour composites, processes for the formation of scaffolds comprised of PGS microparticles, PGS scaffolds formed from such processes, and the use of these PGS microparticles and/or scaffolds for cell and drug delivery applications. These PGS microparticles and/or scaffolds may also be used for cell culture and generation of new tissues.

The present disclosure also relates to the in-situ formation of compositions containing microspherical micro-domains, which may be useful, for example, in creating pressure-sensitive adhesives (PSAs) or other compositions with micro-domains loaded with an active pharmaceutical ingredient.

In some embodiments, processes form particles that include PGS. In some embodiments, processes form a 3-D scaffold from particles that include PGS.

In exemplary embodiments, thermoset microparticles are formed without mold casting. Through combinations of microparticle forming technologies and PGS curing technologies, distinct microparticles and 3-dimensional scaffolds formed from microparticles are created.

In exemplary embodiments, uncured microparticles are dispersed and supported in a continuous phase matrix, typically via suspension. Appropriate energy is applied to the uncured microparticles while they are suspended in the continuous phase matrix to form cured, thermoset substantially spherical microparticles. In some embodiments the energy is heat, electromagnetic radiation (e.g. IR and/or microwave energy) or a combination thereof.

The continuous phase matrix may be any composition that is phase-incompatible with the uncured microparticles and in which the uncured microparticles are supported in their shape until cured. The suspension may occur by any appropriate mechanism, including, but not limited to, shear mixing, induced flow, sonication, or control or adjustment of the specific gravity of the dispersed phase or the continuous phase. When the applied energy is microwave energy, the continuous phase matrix is preferably selected to be transparent to microwaves.

In some embodiments, PGS microparticles and scaffolds are cured through microwaving or other long wavelength electromagnetic radiation, such as IR. PGS has significant sensitivity to microwave energy. This energy may also be used to further sinter/anneal formed microparticles of PGS in proximity to each other. This tunable process may be modified through selective shapes and molds, selective energy processing with microwave dopants, pre-conditioning of irregular shape-to-sphere phase exclusion remodeling, and pre-loading with cells or drugs prior to microwaving.

It will be appreciated however, that PGS microparticles may also be cured by heating, including through conductive and/or convective heating. The heating may be carried out alone or in combination with microwave curing Although methods and compositions are described herein primarily with respect to PGS formed solely from glycerol and sebacic acid, polymeric microparticles from co-polymers of glycerol, sebacic acid, and a third monomer or from non-PGS polymers or co-polymers may also be formed by and used in the present compositions and methods. In some embodiments, a PGS polymer is a co-polymer of glycerol, sebacic acid, and an acrylate, referred to as poly(glycerol sebacate acrylate) (PGSA). In other embodiments, a PGS polymer is a co-polymer of glycerol, sebacic acid, and a urethane, referred to as poly(glycerol sebacate urethane)

(PGSU). If non-PGS polymers are used, those that require elevated temperatures for crosslinking/curing may be preferred.

In some embodiments, the polymer formed into a polymeric microparticle is an ester co-polymer formed from any combination of a poly(ol) and an acid. Appropriate acid monomers may include compounds having one or more acid substituents, including, but not limited to, monoacids, diacids, triacids, tetraacids, and the like. In some embodiments, the acid monomer is a diacid. Such diacids may have the formula [HOOC(CH$_2$)$_n$COOH], where n=1-30. In exemplary embodiments, the diacid includes malonic acid, succinic acid, glutaric acid, adipic acid, pimelic acid, suberic acid, azelaic acid, sebacic acid, or combinations thereof.

Additionally, various non-PGS polymeric compositions may be used in combination with PGS, which may include, but are not limited to, natural polymers, synthetic polymers, or co-polymers of PGS and non-PGS monomers. Microparticles may be formed from such compositions.

Particle Formation

Different methods of microparticle forming technology, which may include, but are not limited to, emulsions, phase-separation, spray drying/congealing, spinning disk atomization, wax coating and hot melt, and freeze drying, may be utilized to form PGS microparticles or core-shell PGS microparticles prior to curing in a continuous matrix phase.

Depending on the materials and conditions, microparticles having a range of physical and chemical properties may be obtained. In some embodiments, the particles are nanoparticle having an average size of less than 1 μm. The PGS may be synthesized with a range of molar ratios of glycerol to sebacic acid, resulting in microparticles having a range of hydrophilicities. In some embodiments, cell culture nutrients are incorporated into the PGS during PGS synthesis, during PGS microparticle formation, or post-loading to improve cell culture capabilities. In some embodiments, oxygen-producing species, such as, for example, magnesium dioxide, may be incorporated into the PGS during PGS synthesis, during PGS microparticle formation, or post-loading to improve oxygenation of culture cells, particularly in dense cell clusters.

Exemplary embodiments can provide for microparticles of PGS or other biodegradable polymers to be created and cured into an elastomer in one continuous step, allowing for the formation of microparticles that retain their spherical shape during thermal curing at elevated temperatures and/or microwave curing.

In some embodiments, concepts of microparticle formation and thermal curing of PGS are utilized and combined into a single step to form crosslinked PGS microparticles. In an exemplary embodiment, the process of making PGS microparticles occurs in a single vessel.

Methods in accordance with exemplary embodiments thus permit easy scale-up of microparticle formation as well as consistent crosslinking densities for all PGS microparticles.

In some embodiments, methods create neat, crosslinked, substantially spherical PGS microparticles (i.e. 100% poly (glycerol sebacate) with no additives) that do not melt at elevated temperatures.

Methods of making PGS particles may be tuned to create microparticles 10, nanoparticles, or larger particles 20, as well as PGS strands 30 and other round configurations of cured PGS, as shown in FIG. 1, FIG. 2, FIG. 3, and FIG. 4. The particle size may be tuned, for example, by adjusting the intensity of shear mixing by adjusting the number of revolutions per minute (RPM), the impeller size and/or shape, and/or the size and shape of the reaction vessel, by adjusting the continuous phase:dispersed phase ratio, by adjusting the viscosity of the continuous phase, by adjusting the viscosity of the dispersed phase, and/or by the absence or presence and amount of emulsifiers and/or stabilizers.

Figure 2:
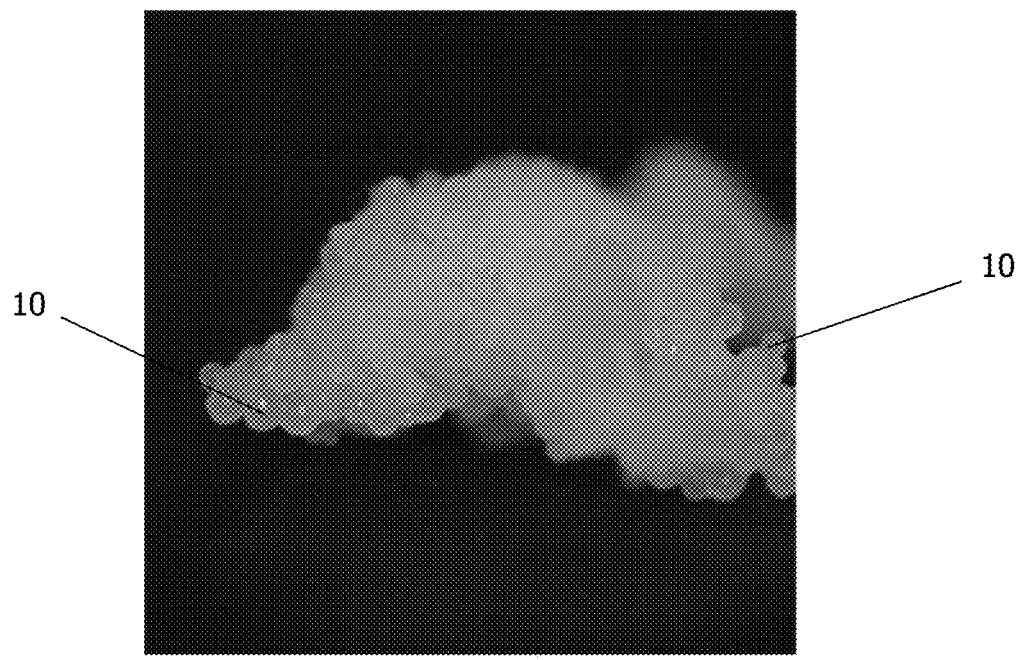
FIG. 2 is an image of a cluster of cured PGS microparticles in an embodiment of the present disclosure.
Figure 3:
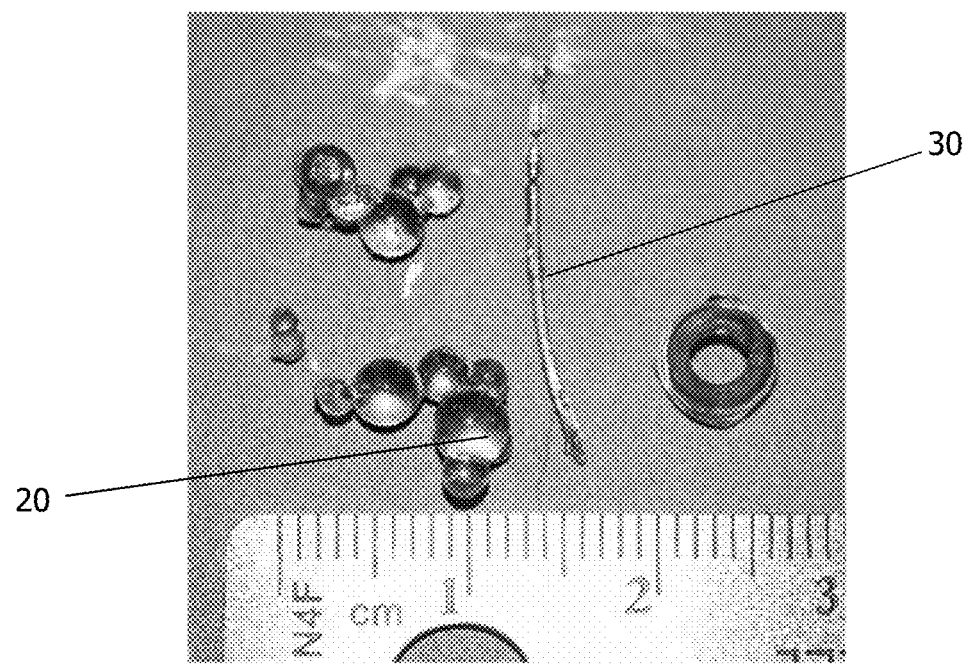
FIG. 3 is an image of different shapes of cured PGS particles in embodiments of the present disclosure.
Figure 4:
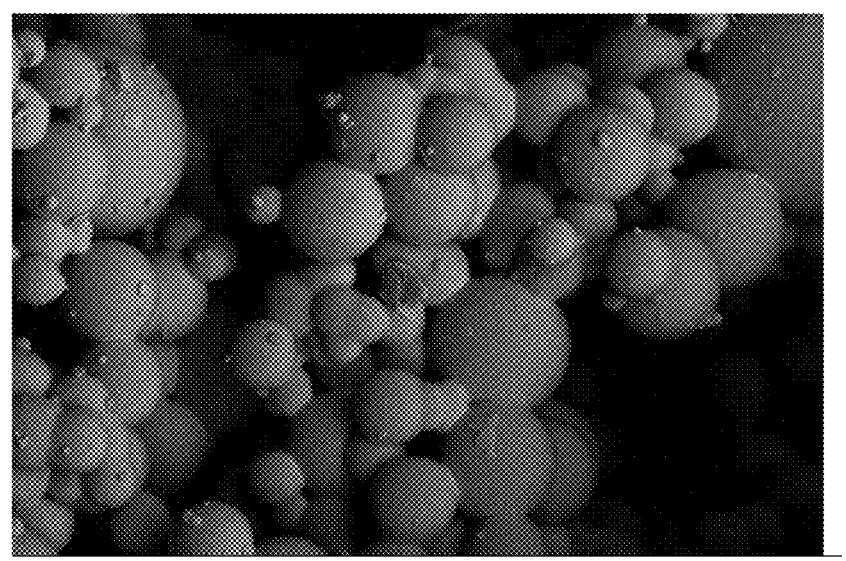
FIG. 4 is an image of PGS microspheres in an embodiment of the present disclosure.

Referring to FIG. 1, the mass of microparticles 10 and the mass of larger particles 20 were formed under similar conditions, with the primary difference being a smaller stir bar producing the larger particles 20. FIG. 2 shows microparticles formed in the presence of monolaurin as a stabilizer. FIG. 3 and FIG. 4 show variations to particle size and shape based on variations to the cure rate and the stir bar.

Methods in accordance with exemplary embodiments have an additional advantage of being able to form microparticles of a narrow particle size distribution.

In some embodiments, the composition of the microparticle includes a PGS resin having a weight average molecular weight in the range of from about 5,000 to about 50,000 Da. In some such embodiments, the resin has a weight average molecular weight in the range of from about 15,000 to about 25,000 Da.

In some embodiments, the microparticle introduced as the dispersed phase is pure resin and in other embodiments a mixture including a PGS resin and a micronized thermoset filler including PGS (sometimes also referred to herein as "flour"). In some such embodiments, the thermoset filler and the resin each have a molar ratio of glycerol to sebacic acid in the range of 0.7:1 to 1.3:1. In some such embodiments, the thermoset filler has a particle size between 0.5 and 1000 μm. In some such embodiments, the thermoset filler has a particle size less than 250 μm. In some such embodiments, the thermoset filler is present in an amount in the range of from about 10% by weight to about 90% by weight of the mixture. In some such embodiments, the thermoset filler is present in an amount in the range of from about 40% by weight to about 70% by weight of the mixture.

In some embodiments, PGS microparticles are formed through shear mixing. While shear mixing is a technique to make microparticles through emulsions, exemplary embodiments maintain the microparticle configuration during shear mixing while thermally curing the microparticles at the same time to form solid, crosslinked, spheroid-shaped PGS microparticles. A spheroid shape is considered to have the least surface area per unit volume and lowest surface energy of a particle in a medium.

Microparticles having a diameter in the range of 1 μm to 1 mm may be formed. In some embodiments, the microparticles have a particle size in the range of 50 μm to 300 μm, alternatively in the range of 100 μm to 500 μm, or any value, range, or sub-range therebetween. The size of the particles may be tuned via the amount of shear mixing as well as the volume ratio of PGS-to-matrix.

In some embodiments, neat PGS microparticles are manufactured by providing a liquid that is phase-incompatible with PGS. The phase-incompatible liquid may be any liquid or viscous medium that is phase-incompatible with the PGS. In some embodiments, the phase-incompatible liquid is non-reactive with the PGS, such as, for example, a mineral oil or a mixture of higher alkanes and/or cycloalkanes. In other embodiments, the phase-incompatible liquid includes one or more compounds that are reactive with the PGS, such as, for example, natural oils, which may include, but are not limited to, olive oil, safflower oil, sunflower oil, canola oil, or combinations thereof. In some embodiments, the phase-incompatible liquid is stirred and heated, such as, for example, to 130° C. (266° F.) for mineral oil, in a reactor vessel that holds vacuum. In still other embodiments, the phase-incompatible liquid may be a base that can be used in forming an in-situ composition, for example an isobutylene or acrylic base for forming an adhesive composition. It will be appreciated that heating is not required and that in some embodiments the processes described herein may be carried out with the phase-incompatible liquid at room temperature.

A vacuum, such as, for example, 10 torr, is applied to the phase-incompatible liquid to remove dissolved gases prior to addition of PGS resin. The vacuum is removed and molten PGS is slowly and directly added to the phase-incompatible liquid, optionally under stirring. This may be accomplished by delivery through a needle, such as shown in FIG. 5, for microparticle formation.

After the PGS resin has been added, the 10-torr vacuum is reapplied and the PGS microparticles are cured, which in one embodiment is achieved by heating in which the mineral oil or other phase incompatible liquid is kept at 130° C. (266° F.) and under stirring to crosslink the PGS. After 24 hours, heating, vacuum, and stirring are removed. The PGS microparticles are then filtered and washed.

Figure 5:
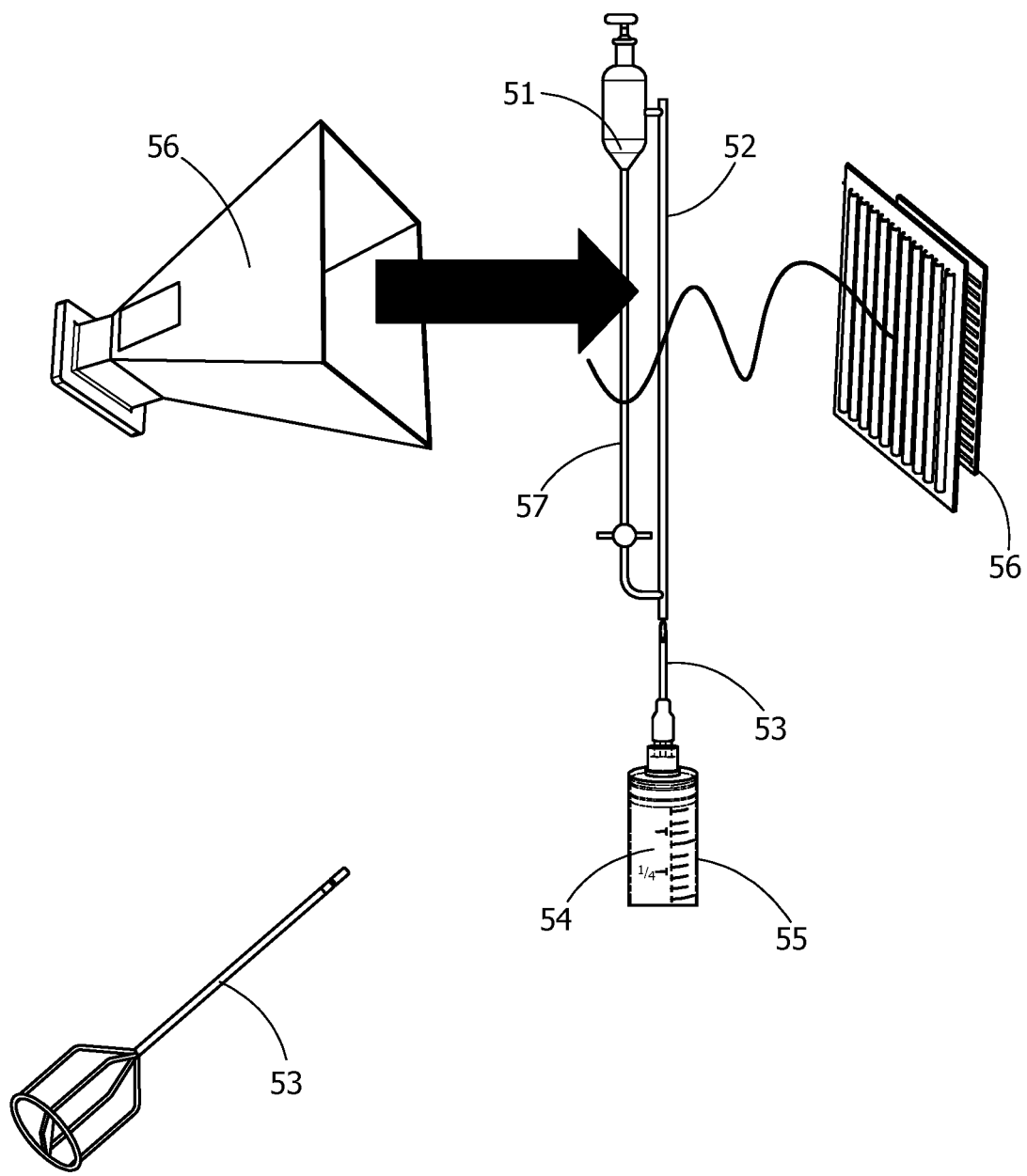
FIG. 5 schematically shows a process for forming microparticles in a vertical column in an embodiment of the present disclosure.

In some embodiments, methods take advantage of specific gravity and buoyancy in a vertical column, such as the one shown in FIG. 5. A phase-incompatible liquid 51 of higher specific gravity than PGS fills a vessel, shown here as a vertical column 52. A tubular delivery fixture 53 at the bottom of the column permits introduction of the PGS resin 54 from a reservoir 55, in the form of a hypodermic needle inserted into the liquid in FIG. 5. The vertical column 52 and reservoir 55 are optionally heated to allow flow.

As illustrated in FIG. 5, the vertical column 52 is surrounded with an appropriate radiation source 56, such as, for example, infrared (IR) or microwave, that is configured to deliver energy through the vertical column 52, the phase-incompatible liquid 51, and the PGS resin 54, with or without heating of the phase-incompatible liquid 51. In embodiments in which a radiation source, particularly microwave, is employed, the phase-incompatible liquid 51 is also selected to avoid dipolar interaction with electromagnetic radiation.

Increasing the needle bore size increases the sphere volume of the PGS resin particles. The lower specific gravity of the uncured PGS resin 54 causes the particles to rise in the vertical column 52. The electromagnetic radiation source 56 cures these particle on the rise. A reversal of the specific gravity ratio may be used to change the direction of the PGS movement. In some embodiments, the system is configured as bleed and feed 57. Exemplary embodiments deliver the molten PGS resin 54 to the hot mineral oil through a needle at a constant rate to create more uniform particle sizes. Created microcylinders of a specific aspect ratio may also be introduced to the vertical column 52 to remodel from cylinder to sphere.

In some embodiments, the average particle size is adjusted by selection of the gauge of the syringe needle forming the resin droplets. In other embodiments, an ultrasonic droplet sonicator may be used in combination with or in lieu of a syringe needle. The average particle size of the PGS resin 54 introduced into the column 52 is adjusted by the sonicator frequency when forming the resin droplets. Increasing the frequency of the sonication decreases the average particle size. It will be appreciated that the vessel does not have to be a column 52 and that the PGS resin can be introduced into the phase-incompatible liquid from the top or bottom of the vessel.

Thus, PGS microparticles having a size of less than 1 millimeter (mm) are formed without the use of a mold, the particles being formed and then cured while suspended in the phase-incompatible liquid of the column 52.

Additives may be included in the continuous phase to form finer particles, to form larger particles, to form a more monodisperse distribution of particle sizes, to help prevent coalescence or flocculation of particles, or a combination thereof. Additives may include, but are not limited to, surfactants, emulsifiers, thickening agents, stabilizers, suspending agents, fatty acids, monoglycerides, triglycerides, polymeric stabilizers, polyethylene glycol (PEG), polycaprolactone (PCL), PEG dimethyl ether, sorbitan esters, polysorbates, polysaccharides, quaternary amines, sodium dodecyl sulfate (SDS), metal oxides, solid nanoparticle stabilizers, natural emulsifiers, lanolin, arabic gum, gelatin, lecithin, or combinations thereof.

The additives may be reactive or non-reactive with the PGS. Additives may be provided in the dispersed phase or the continuous phase. That is, in some embodiments the additives may be mixed into the PGS resin prior to forming the dispersed phase while in other embodiments, additives can be incorporated into the continuous phase to provide a surface coating substantially at or near the surface of the microparticles.

In still other embodiments, the continuous phase can be used as a reversible matrix for the formation of PGS microspheres. PGS microspheres can be formed through known methods as described above. The microspheres are dispersed into a phase-incompatible liquid (continuous phase) that can undergo sol-gel transitions. The continuous phase is then solidified through this sol-gel transition, thus locking the particles into their shape configuration. PGS can then be cured (through heating or microwave) while maintaining their shape. Following cure, the continuous phase is then liquified through the sol-gel transition to free the PGS microparticles.

In certain embodiments, this concept is used to form core-shell microparticles where the core is a phase-incompatible liquid that can undergo sol-gel transitions, and the shell is PGS resin. These core-shell microparticles can be formed through double emulsion processes.

Factors influencing sol-gel transitions include changes in temperature, pH, and non-covalent interactions, such as ionic, hydrogen-bonding, Van der Waals forces. Materials that can be used for the sol-gel transitions include temperature-responsive polymers such as gelatin, poly(NIPAM), and hydroxypropyl cellulose; ionic-responsive polymers such as alginate and chitosan; light-responsive polymers; and various self-assembly and/or supramolecular polymers. a core-shell microparticle is formed from a composition of two phase-incompatible liquids, with one being more energetically favorable to the continuous phase, such as, for example, a PGS-gelatin system.

A method of making PGS microparticles can be achieved through a double emulsion that includes mixing a solution of PGS into an aqueous based stabilizer, such as water and PVA, for example, to create an initial emulsion. The method further includes mixing the initial emulsion into a liquid that is phase-incompatible with PGS, PVA, and water to create a second emulsion.

The phase-incompatible liquid may be stirred at room temperature at the time of mixing; the method further includes heating the mineral oil to greater than 100° C. (212° F.) to drive off solvent, especially water, thereby forming a core-shell microparticle. The method further includes applying a vacuum or reduced pressure and heat in the range of 100° C. to 150° C. (212° F. to 302° F.) to the core-shell microparticles to crosslink the PGS. After about 24 hours, heating, vacuum, and stirring are removed, and the PVA-PGS microparticles are filtered and washed to remove residual oil. The resulting PVA-PGS microparticles can be washed with water to remove the PVA shell, leaving the cured PGS microparticles.

Liquids other than mineral oil may be used as the continuous phase for an emulsion, provided that they are phase-incompatible with PGS and water and are thermally stable at temperatures in the range of 100° C. to 150° C. (212° F. to 302° F.). In some embodiments, temperatures of up to 300° C. (572° F.) may be used to crosslink the microparticles, provided that the continuous phase liquid is thermally stable at those temperatures.

Figure 6:
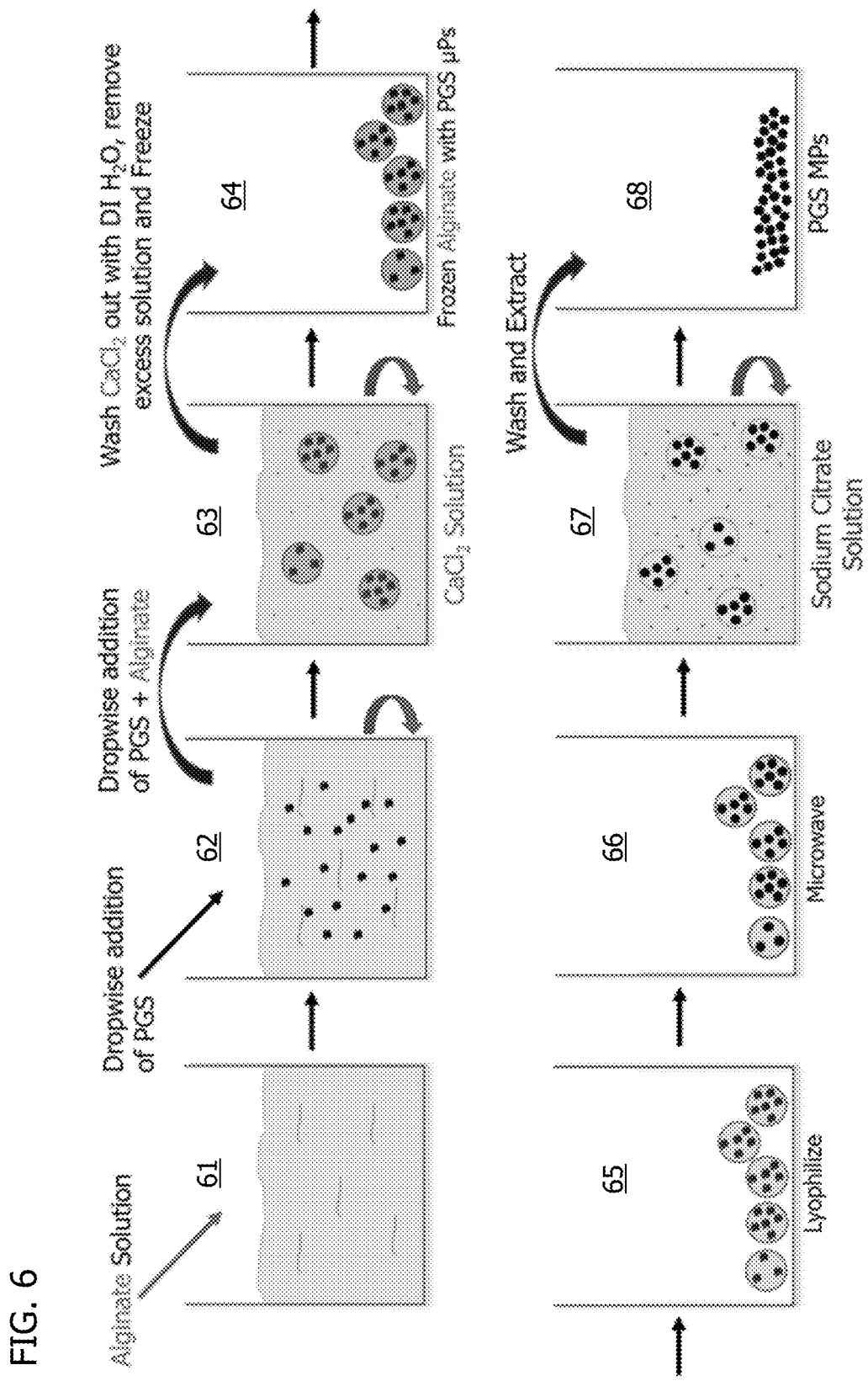
FIG. 6 schematically shows a process for forming PGS microparticles with alginate as an emulsifier in an embodiment of the present disclosure.

In another embodiment, alginate is used as an emulsifying agent for formation of PGS microspheres. FIG. 6 shows an exemplary process. PGS resin in the range of 10 wt % in a solvent up to neat (i.e. 100% wt) PGS resin is added dropwise to an aqueous alginate solution 61. The amount of alginate in the aqueous alginate solution 61 may be any amount that can be solubilized in the aqueous solution, such as, for example, in the range of 0.5 to 4 wt % alginate. Any solvent that solubilizes PGS may be used, including, but not limited to, isopropyl alcohol, ethyl acetate, or tetrahydrofuran. The solvent may be stirred or stagnant at the time of addition.

The addition forms a PGS-alginate-containing solution 62 of initial uncured PGS microspheres. This PGS-alginate-containing solution 62 is added dropwise or continuously to a divalent cation salt solution to rapidly ionically gel the alginate into spheres and form a PGS-alginate-gel-containing solution 63. Appropriate divalent cation salts may include, but are not limited to, calcium chloride ($CaCl_2$), barium chloride ($BaCl_2$), magnesium chloride ($MgCl_2$), strontium chloride ($SrCl_2$), cobalt (II) chloride ($CoCl_2$), cupric chloride ($CuCl_2$), or zinc chloride ($ZnCl_2$). Salts are washed out by multiple rinses of the PGS-alginate spheres using deionized water. The deionized water is then removed, leaving hydrated PGS-alginate spheres.

Figure 7:
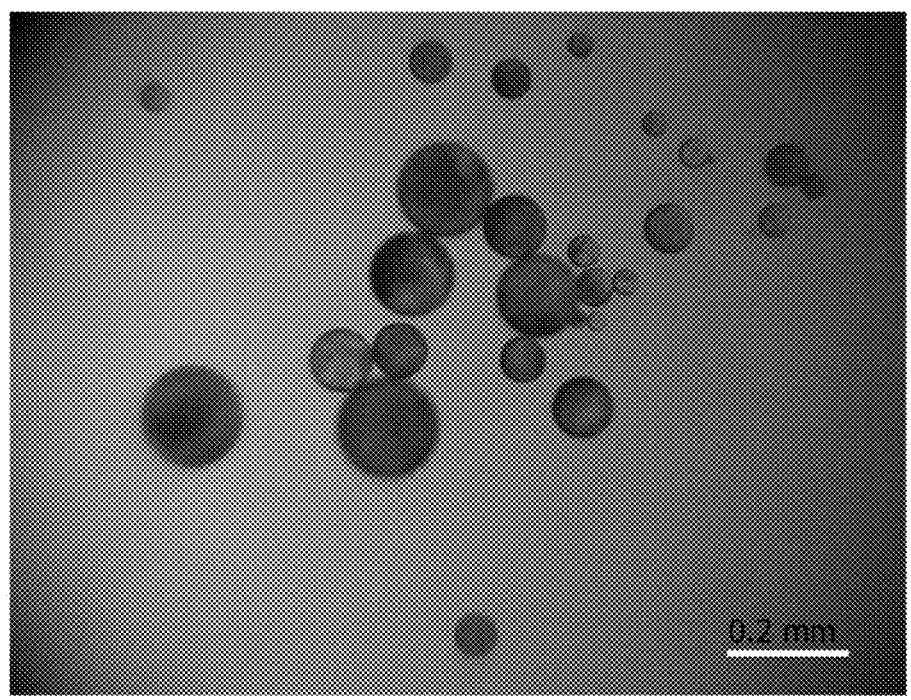
FIG. 7 is an image of PGS microspheres formed by the process of FIG. 6.

The hydrated PGS-alginate spheres are then frozen to form frozen PGS-alginate spheres 64. The frozen PGS-alginate spheres 64 are then lyophilized to form dry PGS-alginate spheres 65. The dried PGS-alginate spheres 65 are then cured to crosslink the PGS microspheres forming cured, alginate-entrapped PGS microspheres 66. Appropriate curing processes may include, but are not limited to, microwaving, heating in an oil, or heating in a vacuum oven. The cured, alginate-entrapped PGS microspheres 66 are placed into an alginate-chelating solution, which may be stirred or stagnant at the time of addition, to chelate the divalent cation away from alginate. This reverses the alginate crosslinking, which allows the alginate to degrade, releasing the cured PGS microparticles from the alginate to form a cured PGS microparticle-containing solution 67. Appropriate alginate chelators in the alginate-chelating solution may include, but are not limited to, sodium citrate, 1,2-bis(o-aminophenoxy)ethane-N,N,N',N'-tetraacetic acid (BAPTA), ethylene glycol-bis(β-aminoethyl ether)-N,N,N', N'-tetraacetic acid, (EGTA), and/or ethylenediaminetetraacetic acid (EDTA). Alternatively, an enzyme, such as, for example, alginate lyase may be used to degrade the alginate and release the cured PGS microparticles. The cured PGS microparticles are then concentrated, such as, for example, by centrifugation, and washed multiple times to remove residual degraded alginate and sodium citrate salts prior to drying and storage of the final PGS microparticles 68. FIG. 7 shows microspheres made by such a process.

The average particle size and range of the PGS microparticles may be tuned by adjusting one or more parameters of the process, which may include, but are not limited to, the weight percentage of the alginate, the stirring speed (shear rate), the weight percentage of PGS, the use of a surfactant, and the solvent (or lack thereof) used with PGS resin.

In some embodiments, the continuous matrix phase for formation of cured microspheres is a base for in-situ formation of a composition containing suspended cured microspheres. For example, in some embodiments the continuous matrix phase is an elastomer. The elastomer may be a polymer used with PGS to form a PSA. In some embodiments, the elastomer is acrylic-based. In other embodiments, the elastomer is isobutylene-based. The uncured dispersed microspherical micro-domains of PGS may be cured by microwave or conductive heating to form cured microspheres. The phase-incompatible material for the base material for the continuous phase may be selected to be substantially invisible to microwave (i.e. having little or no dipole moment), the continuous phase resists curing such that the resulting composition can still exhibit some viscous flow even after the dispersed microparticles have cured.

The use of PGS as spherical microdomains within a base composition may be used in formulations for bioresorbable controlled release of actives and biologics delivered to the skin. In microstructures where the PGS domains acts like a particle, the controlled release structural domain as well as a component to a pressure-sensitive adhesive (PSA) may mean a different approach to formulating an active PSA, rather than considering the component merely as a service component to a wound care PSA adhesive. In some embodiments, PGS micro-domains contain APIs for wound care in a controlled release construct and contribute to adhesion of a PSA.

PGS has inherent antimicrobial and non-immunogenic features in tissue engineering. Patients suffering from chronic wounds, like diabetic ulcers, have compromised immune systems and often have an allergic reaction to PSAs commonly found in wound care dressings, which may further damage the fragile skin of older patients leading to infection and other complications.

When PGS is blended with an elastomer of a typical transdermal material to form a PSA, the PGS forms microspherical structures in an elastomer matrix under certain conditions. The PGS functionally contributes to the physical tack but may be independently formulated with an API or other controlled release agents before it is formulated into the elastomer. In such cases, these microspheres may act to provide controlled release, while still contributing to the physical tack of the PSA. In chronic wounds, for example, an antibiotic or trophic agent may be provided as the controlled release agent to improve healing from the perimeter of a wound. The PGS or the PSA composition may serve as another construct concept for transdermal drug delivery. Essentially the development of the microsphere simultaneously results in the PGS microsphere acting as both as a functional PSA component and a delivery vehicle.

In some embodiments, a method of forming a pressure-sensitive adhesive composition includes combining a polymeric ester with one or more controlled release agents to form an ester phase. The combining loads the polymeric ester with the controlled release agent. The method further includes combining the ester phase with an elastomer phase including an elastomeric polymer. The ester phase and the elastomer phase are combined at a ratio which produces a discontinuous microspherical ester phase in a continuous elastomeric phase matrix to form a pressure-sensitive adhesive composition. In some embodiments, the ester includes PGS. In some embodiments, the elastomer includes polyisobutylene (PIB). In some embodiments, the elastomer includes an acrylic.

Controlled release agents for PSAs may include, but are not limited to, wound care agents, nutritional doping/bioactive agents, API agents, biologic agents, drug agents, gene transfer technology agents, co-polymer particle development agents, or island agents in the sea matrix dissolution. Wound care agents may include, but are not limited to, trophic agents, hemostatic agents, antibiotics, antimicrobials, analgesics, APIs, ointments, alginates, hydrogels, fillers, deodorants, Manuka honey, growth enhancers, or stimulants.

In some embodiments, a method includes applying a pressure-sensitive adhesive composition to a substrate to form a pressure-sensitive adhesive device. In some embodiments, the pressure-sensitive adhesive device is a wound care dressing. In some embodiments, a method includes applying a pressure-sensitive adhesive device to a target surface. The pressure-sensitive adhesion composition has sufficient tack to adhere the pressure-sensitive adhesive device to the target surface. The controlled release agents are predominantly associated with the microspherical ester phase of the pressure-sensitive adhesive composition and are released at the target surface over time in a controlled manner from the pressure-sensitive composition.

Although methods and compositions are described herein primarily with respect to PGS as the ester component in an ester:elastomer PSA, non-PGS esters may alternatively serve as an ester component in a PSA formed by the present methods. In some embodiments, the ester component is biodegradable. In some embodiments, the ester is a co-polymer formed from any combination of a poly(ol) and a diacid.

As previously mentioned, some embodiments include a micronized thermoset PGS filler mixed into the PGS resin used to form the microparticles while in other embodiments, previously formed filler particles, which may be of irregular shape, may be remodeled into spherical form.

The crosslink density of the filler may be as low as 0.00 mol/L up to about 0.07 mol/L or greater. The crosslink density is calculated with respect to the thermoset material prior to particularization by soaking samples in tetrahydrofuran for 24 hours to obtain a swollen mass, dried until a constant dry mass is acquired (typically about 3 days) and the swelling percentage is then used to calculate the crosslink density using the Flory-Rehner expression for tetrafunctional affine networks. A lower crosslink density, which may be as low as 0.00 mol/L, indicating no or minimal crosslinking, allows for "sintering" or annealing when curing/microwaving the flour particles.

According to such embodiments, sprayable formulations include a mixture of PGS including a resin of glycerol-sebacic acid ester, and thermoset PGS that has been processed into a flour or powder of fine particle size. Mixtures of PGS resin and micronized thermoset PGS are described in U.S. Pub. No. 2017/0246316 and U.S. Pub. No. 2018/0050128, both of which are hereby incorporated by reference.

In some embodiments, cast and partially-cured PGS thermosets are cryo-milled to form PGS flour. The PGS thermosets particles are partially cured with enough sol fractions to permit remodeling. PGS flour is a micronized polymer of PGS forming a powder or "flour" consistency. This PGS flour is composed of non-spherical, irregular-shaped microparticles that are generally less than 1000 µm in size.

The PGS thermoset may then be further cured to different degrees of crosslinking, thus resulting in PGS flour with varying amounts of thermoplastic sol fraction. PGS flour with sufficient amounts of thermoplastic fraction may then be remodeled, by melting of the sol fraction, to make PGS microparticles with rounded edges through curing techniques for PGS, such as, for example, microwaving and/or high heat and vacuum.

In some embodiments, PGS flour particles are modified for a different particle size distribution or geometric shape variation or loaded or coated with one or more controlled release agents, which may include, but are not limited to, nutritional doping/bioactive agents, API agents, biologic agents, drug agents, gene transfer technology agents, co-polymer particle development agents, or island agents in the sea matrix dissolution. Any appropriate loading of controlled release agents may be used, such as, for example, up to 60 wt % or up to 70 wt %. In some embodiments, the controlled release agent does not react with the PGS polymer during curing.

Depending on the crosslinking extent of PGS flour particles, they may be remodeled into microparticles with a more rounded or spherical configuration, including methods, such as, for example, phase exclusion particle remodeling in a phase-incompatible liquid or microwave remodeling in a non-dipole liquid or solid.

In some embodiments, a method includes making 100% solids powder coating films using PGS flour and sintering/annealing particles with microwave or IR energy to encourage sintering/annealing and flow and leveling. PGS particles that have been crosslinked for less than 48 hours at 120° C. (248° F.) and 10 torr have sufficient lower molecular weight thermoplastic PGS fractions for remodeling. The method includes particle sintering/annealing with coherent and/or non-coherent radiant energy and/or with superheating in a liquid or non-oxidizable gas-plasma.

In some embodiments, a method of making PGS microparticles through PGS flour remodeling includes mixing PGS flour particles into mineral oil at room temperature under stirring to evenly disperse the flour particles. The method also includes heating the mineral oil to greater than 50° C. (122° F.) to remodel the thermoplastic fractions of the flour particles. The method further includes applying a vacuum or reduced pressure and heat in the range of 100° C. to 150° C. (212° F. to 302° F.) to the remodeled PGS to crosslink the PGS. After about 24 hours, heating, vacuum, and stirring are removed, and the PGS microparticles are filtered and washed to remove residual oil.

The various methods described herein for the formation of microparticles are also amenable to macroparticle development, including macroparticles having a diameter up to 3 mm, and even up to about 2 centimeters (cm) in diameter. In macroparticle structures of PGS, the materials may be incorporated into engineering polymers to enhance impact resistance, additive carrier systems, and forms that subsequently act as fusible fillers into void spaces.

In some embodiments, a method to prepare microcylinders for remodeling includes a die template to "punch" out cylinders for remodeling or for addition to a vertical column.

PGS microparticles formed in accordance with exemplary embodiments may be used for cell technologies and drug delivery applications. In some embodiments, PGS microparticles are loaded with controlled release agents, such as, for example, drugs. The PGS microparticles can serve as drug and cell delivery vehicles, utilizing the innate elastomeric, immunomodulatory, and antimicrobial nature of PGS without additional additives. In drug delivery applications, drugs may be add-mixed into the PGS resin before microparticle formation as a controlled release agent, and/or drugs may be loaded onto microparticles after formation, including by surface coating as described.

In some embodiments, the PGS microparticles are coated or loaded with one or more drugs. In some embodiments, the PGS microparticles are coated with cell adhesion moieties or proteins to improve cell culture.

Distinct lots of microparticles may be synthesized with varying drug loading concentrations or types of drugs. These distinct lots may be mixed or combined in different ratios to deliver various drugs with varying release kinetics.

In some embodiments, the PGS microparticles are used in a cell delivery application. The microparticles may be used as a cell adhesion substrate for cell delivery. Aggregated microparticles may be used as a porous 3-D scaffold for cell delivery. Biodegradable PGS microparticles may serve as a temporary substrate for cell attachment, allowing for eventual cell-cell aggregation. This is important as cells behave differently as aggregates (3-D culture) than when adhering to a flat substrate (two-dimensional culture).

In some embodiments, PGS microparticles serve as at least part of a degradable substrate for cell culture, proliferation, differentiation, adhesion, and cluster formation. In some embodiments, PGS microparticles serve as a cell delivery vehicle. The physicochemical properties of PGS may be tuned through crosslinking extent or post-treatment to alter the biocompatibility of the PGS microparticles and tune cell culture capabilities. In some embodiments, clusters of PGS microparticles, either via PGS scaffolds from microparticles or cell clustering, as shown in FIG. 4, FIG. 10A-10C, FIG. 11, and FIG. 12, for example, are used as a degradable scaffold for tissue formation and cell therapy. In some embodiments, clusters of PGS microparticles are incorporated into a larger capsule to form a tissue/organ-forming "seed".

In some embodiments the PGS microparticle can be made in the 3-10 μm range, which is the size range of red blood cells (RBC). As the PGS microparticle is elastic it can mimic the elastic and deformation characteristics of RBC's allowing for the ability to pass through the capillary bed. The ability to create an elastomeric and deformable 3-10 μm microparticle also can be used to provide a parenteral, intravenous or cardiovascular drug delivery system that could circulate, and control release a material formulated into the PGS microparticle.

Other medical applications may include in vertebral disc replacement, in spinal spacers for polymers, or in cancer hyperthermia treatment.

For cartilaginous applications such as vertebral disc or meniscal repair or replacement, microparticles derived from rigid plastic-like lactides and glycolides have the disadvantage of being rigid and exhibiting bulk-eroding degradation kinetics. The rigidity of these materials results in compliance mismatch with that of the cartilaginous tissue and the bulk eroding characteristics results in uncontrolled loss of mechanical properties and unpredictable release kinetics. PGS microparticles are geometrically stable in aqueous environments because of the surface erosion feature, resulting in controlled loss of mechanical properties accompanied by zero order release kinetics. Therefore, a major advantage of this invention is the development of an elastomeric, zero-order release microparticle useful, for instance, in joint spaces and confined tissue structures.

Such a feature and property provide a major advantage for controlled release active delivery in applications where joint space disease could benefit from a controlled release therapy. For instance, an elastomeric microparticle formulated with an anti-inflammatory or stem cell composition injected into a joint space will likely not cause abrasion or surface damage to epiphyseal surfaces during the therapeutic period. The same would be true for tissues where compression is part of the normal physiological function such as muscle and tendons.

Furthermore, in compressive joint spaces delivery of a microsphere or microparticle through a small-bored delivery device such as a needle or cannula to a specific lesion or targeted site in combination with a PGS based adhesive such as PGSA or PGSU or PGS/OGS, would provide a method for in situ surface remodeling or site-specific therapy.

For cancer hyperthermia treatment, localized heating is used to damage and kill cancer cells at a cancer hyperthermia therapy site, such as, for example, a tumor site. Microparticles or a scaffold of microparticles containing an exogenously-excitable polymeric material are placed at the tumor site. Exogenous energy then excites the exogenously-excitable polymeric material at the cancer hyperthermia therapy site to heat the cancer hyperthermia therapy site to a hyperthermia temperature. Appropriate exogenous energy may include, but is not limited to, microwave energy, radiofrequency energy, terahertz energy, mid-infrared energy, near-infrared energy, visible energy, ultraviolet energy, X-ray energy, magnetic energy, electron beam energy, or a combination thereof. In some embodiments, the exogenously-excitable polymeric material is PGS. In some embodiments, the microparticles are loaded with one or more chemotherapeutic agents. The biodegradable, biocompatible microspheres degrade over time and therefore do not need to be removed from the cancer hyperthermia therapy site after the therapy.

Both neat PGS and PGS compounded with spheroids may be used in subterranean exploration as for instance in sealing and gasket technologies, such as where a flexible biodegradable gasket may be advantageous.

Other uses of PGS microparticles may include, but are not limited to, in toys, as a polymer additive for impact resistance, for additive delivery, for food flavors, or as elastic fillers.

Scaffold Formation

In some embodiments, a 3-D PGS structure or scaffold is formed from PGS microparticles. In some embodiments, PGS microparticles are sintered together to form a macro-PGS structure/scaffold. PGS microparticles may be coated in a PGS resin-based glue to improve sintering, especially if the microparticles have limited thermoplastic fractions to remodel. The microparticles used in scaffold formation may be spherical microparticles formed in accordance with the embodiments described herein, irregular shaped microparticles (including PGS flour particles), or a combination thereof.

In some embodiments, variation to the size of the microparticles is used to tune porosity and pore size of the scaffold. Degradable and/or leachable porogens may be incorporated to further tune porosity and pore size, as well as other fugitive materials. In some embodiments, a scaffold of PGS microparticles includes a microwave dopant, such as, for example, biodegradable silica.

PGS flour particle size may dictate pore size and shape. The PGS flour may be remodeled into spheres for microwave sintering/annealing using phase exclusion liquid or heated gas remodeling to achieve a desired porosity or pore size. Also, different degrees of polymerization of the PGS flour offer different energy inputs for different microwave remodeling. In some embodiments, PGS flour is shape-molded into tissue scaffold structures. In some embodiments, PGS flour particle size variations include a composition creating a plurality of pore sizes or as a singular particle size to create a narrow pore size distribution.

In some embodiments, spherical PGS particles establish a cell scaffold template. For example, aggregates of PGS microparticles may be formed to create porous 3-D structures, as shown schematically in FIG. 8. While described primarily with respect to spheres, the particle shape is not so limited and may include other geometric forms resulting from the process configuration and set-up.

Figure 8:
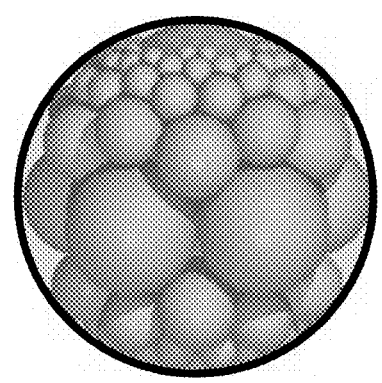
FIG. 8 is a schematic capsule of microparticles with interspheroid void spaces in an embodiment of the present disclosure.

Different distinct lots of microparticles (e.g. different sizes and/or composition) may also be combined to form scaffolds as seen in FIG. 8. The scaffolds are then able to release a multitude of drugs without having to incorporate every drug into each microparticle. In regenerative medicine applications, patterned or ordered complex tissue growth may be dictated by combining distinct lots of microparticles in separate regions. Distinct lots of microparticles may also be combined to form a gradient or gradients of drugs in a scaffold. Similarly, distinct lots of microparticles may be used to culture different cell types. A patterned or gradient configuration of these microparticle-cell conjugates may then be constructed in a scaffold to derive complex tissue/organ formation.

Selection of a plurality or specified selection of PGS thermoset micronized particles may be made to modulate porosity and topology under various radiant energy processes.

In some embodiments, a method of forming a scaffold incorporates the concept of "lost-wax" or cire perdue so that the organ-scaffold shape including unusual anatomical topology is held together with a fugitive binder, such as polyvinyl alcohol or paraffin, that is removed following the microwave sintering/annealing of the PGS flour particles.

Figure 10A:
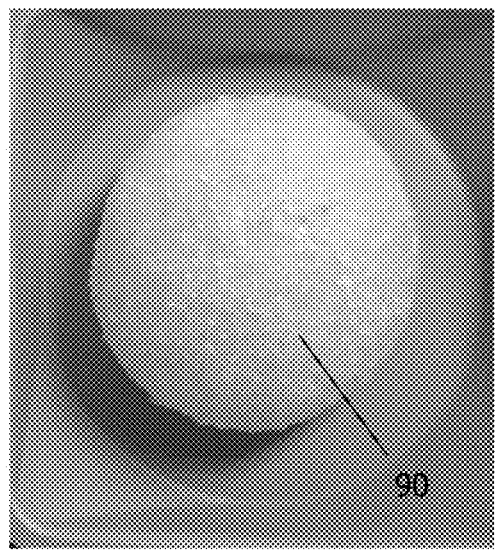
FIG. 10A is an image of a hollow sphere of molded and cured PGS flour particles in an embodiment of the present disclosure.
Figure 10B:
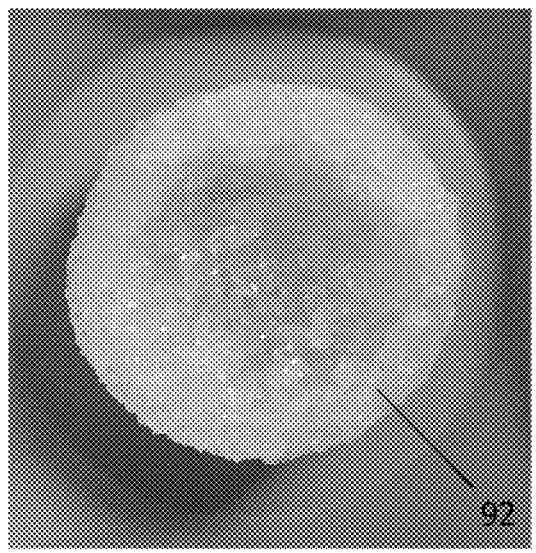
FIG. 10B is an image showing the hollow core of half of the hollow sphere of FIG. 10A after breaking apart the hollow sphere of FIG. 10A.
Figure 10C:
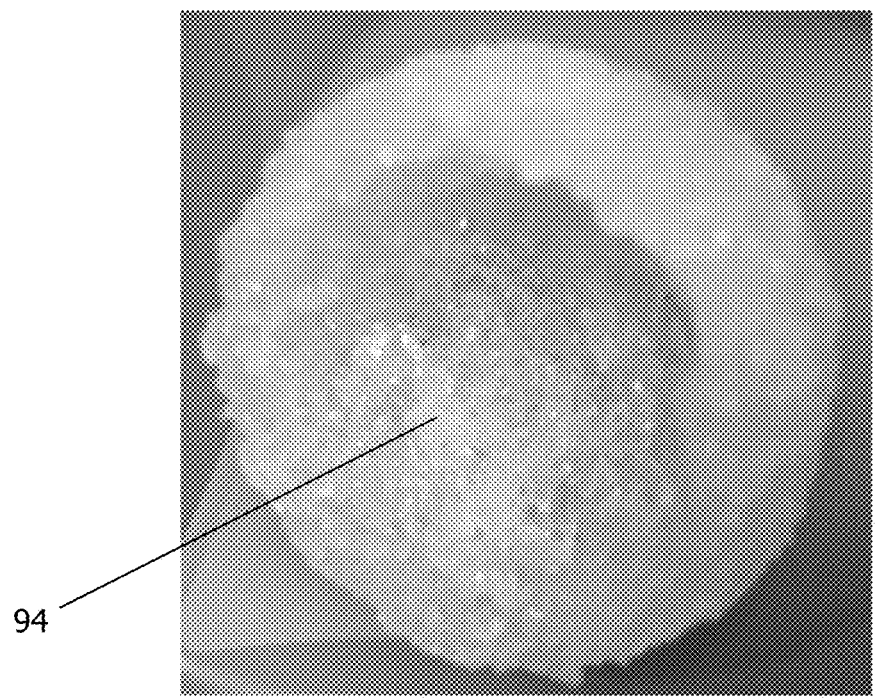
FIG. 10C is an image of another view of the half of the hollow sphere of FIG. 10B.

A scaffold having a spherical shape 90 is shown in FIG. 10A; the scaffold is formed from PGS flour in a shell 92 around a hollow core 94, as shown in FIG. 10B and FIG. 10C.

Figure 11:
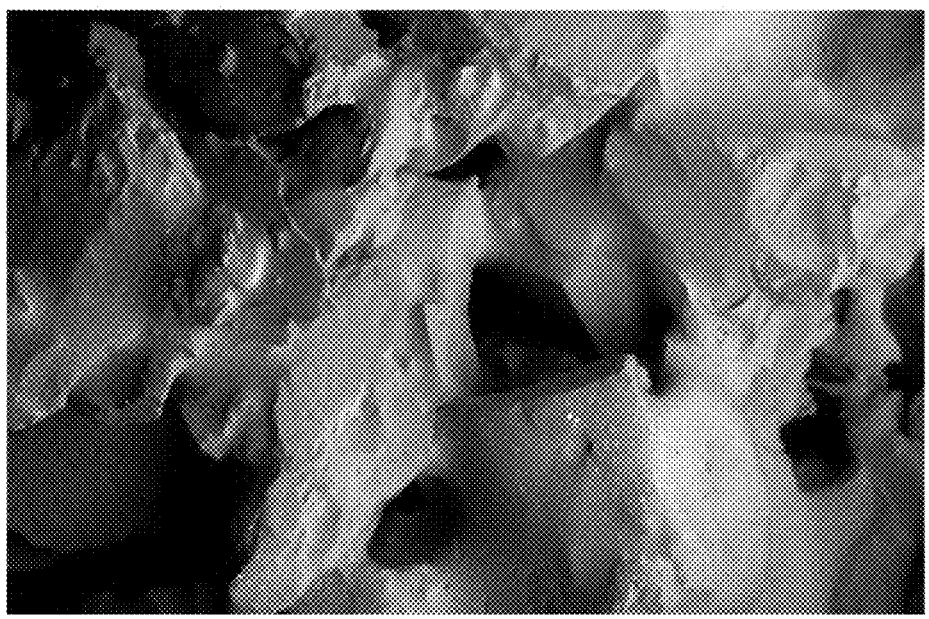
FIG. 11 is an image of a portion of the surface of the hollow sphere of FIG. 10A after microwaving the PGS flour particles.

In some embodiments, a method of making a PGS scaffold from microparticles includes combining and shaping PGS microparticles, either as a free-standing structure or packed into a mold. The method also includes sintering/annealing and curing the microparticles via high heat and vacuum or via microwaves to produce a scaffold of PGS with pores, as shown in the image of FIG. 11 of PGS flour after sintering/annealing and curing, which is a magnified view showing the microstructure of the scaffold of FIG. 10A.

The pore-scaffold porosity may be dictated by PGS flour particle size or inclusion of fugitive materials that can be removed either during microwaving or as a separate process.

The raw flour may be modified to affect the properties of the resulting scaffold. The particle size distribution of the PGS flour modulates the porosity. Such modifications may include, but are not limited to, geometric shape variations, providing nutritional doping or bioactive agents to the particle, providing API or biologic agents, providing gene transfer technology agents, providing co-polymer development particle development agents, or providing island agents in the sea matrix dissolution.

The microwave process may also be modified to affect the properties of the resulting scaffold. Such modifications may include, but are not limited to, selective shapes and molds, selective energy processing with microwave dopants, pre-conditioning of flour-to-sphere phase exclusion remodeling, or pre-loading of cells.

In some embodiments, spherical PGS microparticles and/or irregularly shaped PGS flour particles serve as a base for a scaffold in the form of a mini-implantable bioreactor. In some embodiments, the PGS microparticles are microwave-annealed into a capsular shape having a hollow center and a modulated wall porosity. The particle size, sintering/annealing energy, and sintering/annealing time are selected to modulate the pore size through the capsule wall. The hollow center of the capsule is a "cell bed" for cell media and cells to expand in situ. The microparticles may be fortified with nutrients and/or oxygenation entities. A supporting capsular periphery may be further "hardened" by thermal methods to provide an implantable capsule. The capsule size may be selected based on the requirements for the implant.

Figure 12:
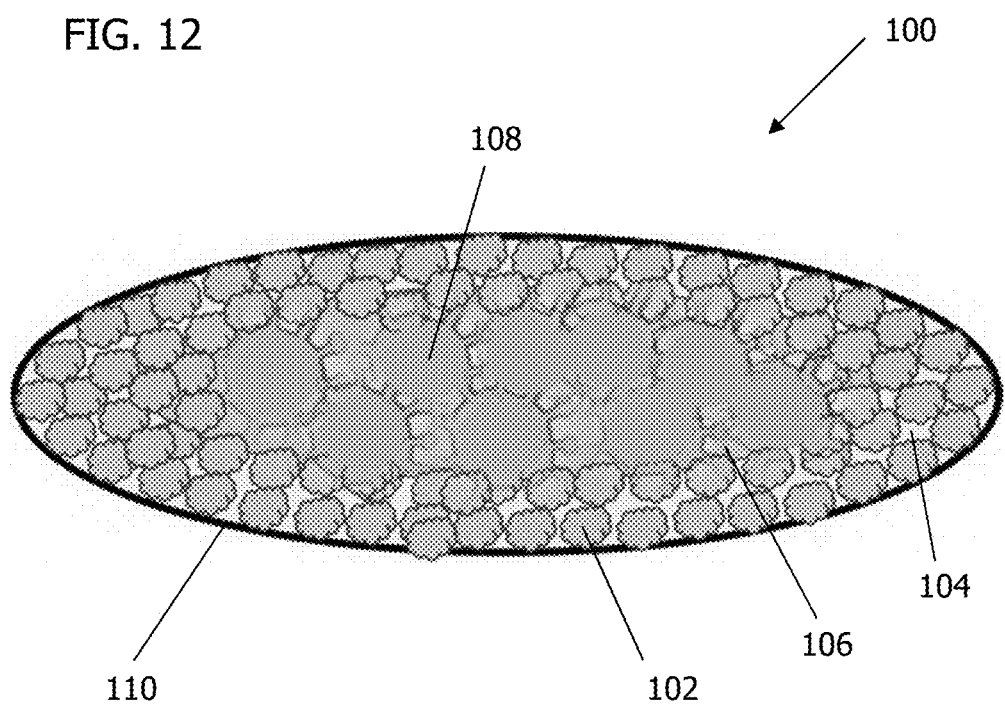
FIG. 12 schematically shows a mini-implantable bioreactor.

A mini-implantable bioreactor 100 formed from PGS particles may be spherical or egg-shaped (ovoid), as shown schematically in FIG. 12. The PGS microparticles 102, which may be PGS flour microparticles, form an outer shell defining the general shape of the mini-implantable bioreactor 100 with interstitial space and porosity 104 between PGS microparticles 102. The hollow capsular core 106 defined by the PGS microparticle 102 shell holds cells 108 in a cell culture. The mini-implantable bioreactor 100 may further include an extra-peripheral support film or annealing "skin" 110. This annealing skin 110 may be post-processed by laser ablation to provide through-holes in the annealing skin 110. The mini bioreactor 100 may be a transfer capsule of expanded cells 108 for cell therapy based on PGS microparticle technologies.

In some embodiments, PGS flour particles are processed into a film from a powder. Target objects may be PGS-coated similar to powder coating, such as a microwave PGS flour powder coating. In some embodiments, a substrate is powder-coated with flour particles. In some embodiments, a 3-D scaffold is designed for an entire organ system as a mold filler or as a composition containing flour that is exposed to microwave energy following shaping. In some embodiments, a method of "lost-wax" or cire perdue forms the organ-scaffold shape, including an unusual anatomical topology, with the shape being held together with a fugitive binder, such as, for example, polyvinyl alcohol or paraffin, that is removed following the microwave sintering/annealing of the PGS flour particles.

EXAMPLES

The invention is further described in the context of the following examples which are presented by way of illustration, not of limitation.

Example 1

200 mL of heavy mineral oil was heated to 130° C. (266° F.) in a reactor vessel under stirring with a magnetic stir bar (400 RPM), and a vacuum (10 torr) was applied to the mineral oil to remove dissolved gases. The vacuum was removed and 2 mL of molten PGS was slowly added directly to the hot mineral oil under stirring through a syringe with an 18-gauge (18 G) needle. After the PGS resin was added, the 10-torr vacuum was reapplied and the PGS microparticles were maintained at 130° C. (266° F.) and under stirring to cure the PGS. After 20 hours, the heat, vacuum, and stirring were removed. The cured PGS microparticles were then washed and collected. FIG. 1 shows microparticles 10 and 20 formed by Example 1 using different shear rates resulting from different sized stir bars (lower shear rates result in larger sized microparticles).

Example 2

200 g of heavy mineral oil was mixed with 6 g of monolaurin and heated to 130° C. (266° F.) in a reactor vessel under stirring with a magnetic stir bar (400 RPM), and a vacuum (10 torr) was applied to the mineral oil and monolaurin mixture to remove dissolved gases. The vacuum was removed and 1 mL of molten PGS was slowly added to the hot mineral oil under stirring through a syringe with an 18 G needle. After the PGS resin was added, the 10-torr vacuum was reapplied and the PGS microparticles were maintained at 130° C. (266° F.) and under stirring to cure the PGS. After 20 hours, the heat, vacuum, and stirring were removed. The cured PGS microparticles were then washed and collected. FIG. 2 shows the microparticles 10 formed by Example 2.

Example 3

PGS microspheres were formed by emulsion with alginate as an emulsifying agent. PGS resin at 50 wt % solubilized in 99% isopropyl alcohol was added dropwise to an aqueous solution of 1 wt % alginate with stirring of the alginate solution at the time of addition to form uncured PGS microspheres. The PGS-microsphere-containing alginate solution was added dropwise to a 90 millimolar (mM) $CaCl_2$ solution to rapidly ionically gel the alginate into spheres containing the uncured PGS microspheres. The alginate spheres were washed multiple times with deionized water to remove the excess calcium chloride. The deionized water was then removed, leaving hydrated PGS-alginate spheres.

The hydrated PGS-alginate spheres were then frozen. The frozen PGS-alginate spheres were then lyophilized to remove the water. The dry PGS-alginate spheres were then microwave-cured for two minutes at an intermediate power in an inverter microwave oven to crosslink the PGS microspheres, thereby forming cured, alginate-entrapped PGS microspheres. The cured, alginate-entrapped PGS microspheres were then placed into a 135 mM sodium citrate solution that was stirred at 400 RPM for one hour to chelate the divalent cations away from the alginate. This reverses the alginate crosslinking and causing the alginate to degrade, releasing the cured PGS microparticles from the alginate. The cured PGS microparticles were then concentrated by centrifugation and washed multiple times with deionized water to remove residual degraded alginate and sodium citrate salts prior to drying and storage of the final PGS microparticles.

FIG. 7 shows an image of final PGS microparticles post-cure in deionized water, as prepared by the PGS-alginate synthesis process of Example 3. The PGS microparticles have an average size of 79.3 µm, covering a range from 14.3 µm to 169.3 µm.

Example 4

PSA formulation hand sheets were prepared using poly (glycerol-sebacate) (PGS) resin formulated with a commercially available polyisobutylene (PIB) resin. PSA formulations were prepared with elastomer(PIB):ester(PGS) ratios of 25:75 w/w, 50:50 w/w, and 75:25 w/w.

The PSA formulations were imaged by an LDIR microscope (Agilent Technologies, Santa Clara, Calif.), a commercially available imaging microscope (PerkinElmer, Inc., Waltham, Mass.), and an FT-IR spectrometer commercially available under the Stingray trade name (DigiLab, Inc., Hopkinton, Mass.).

Figure 9C:
FIG. 9C is an LDIR image of a 75:25 elastomer:ester pressure-sensitive adhesive system.
Figure 9B:
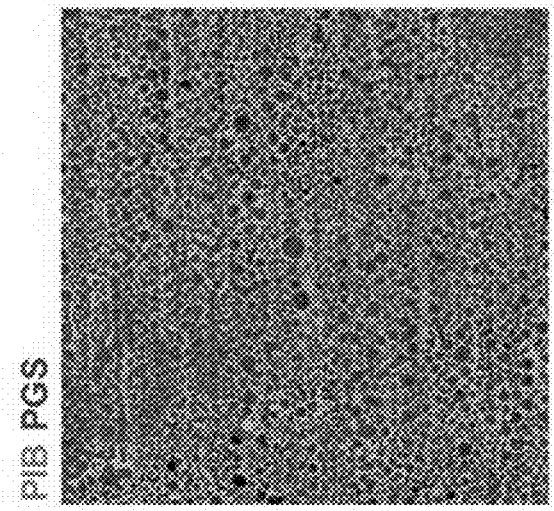
FIG. 9B is an LDIR image of a 50:50 elastomer:ester pressure-sensitive adhesive system.
Figure 9A:
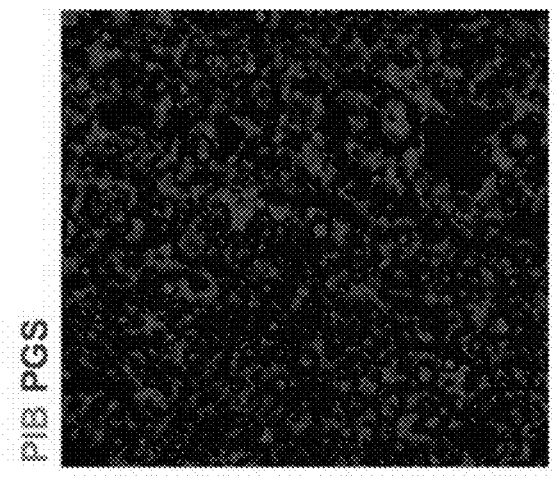
FIG. 9A is a laser-directed infrared (LDIR) image of a 25:75 elastomer:ester pressure-sensitive adhesive system.

FIG. 9A, FIG. 9B, and FIG. 9C show the resulting LDIR images for the 25:75 w/w, 50:50 w/w, and 75:25 w/w elastomer:ester ratio PSA formulations, respectively. The light represents the PGS, whereas the dark represents the PIB. The LDIR images show the phase inversion in both the 25:75 and 75:25 samples. Only the 50:50 PSA formulation showed an aggregate of both components at the surface. The 50:50 PSA formulation had the highest tack of the three formulations.

Example 5

A sample of a commercially available proprietary acrylic PSA wound care adhesive was formulated with PGS to form a releasable PSA formulation.

The release of the PSA adhesion from the skin for this releasable PSA formulation is facilitated by the design of the PSA carrier film. Laser-drilled micropore through-holes in the PSA carrier film provide an open vertical conduit to the bulk adhesive from the dressing top-side. To remove the PSA, IPA is swabbed over the perforated carrier. The IPA then wicks down through the micropore holes to penetrate the bulk film.

Example 6

Flour particles were made from PGS thermosets that were cured for 24 hours in a vacuum oven (120° C., 10 torr). The thermosets were snap-frozen with liquid nitrogen and crushed into small pieces less than 1 cm in size. The pieces were then cryoground into fine particles less than 500 µm in diameter. To sinter flour particles together, the flour particles were packed in close proximity and microwaved to enable remodeling of the particles.

To create porous, 3-dimensional structures from flour particles, the particles were packed around a ceramic bead. The particles and ceramic bead were then microwaved to sinter the flour particles together. The ceramic bead was removed, and the sintered particles were then further crosslinked in a vacuum oven (120° C., 10 torr) for 15 hours to create a tack-free scaffold, as shown in FIG. 10A, FIG. 10B, and FIG. 10C.

Example 7

Figure 13:
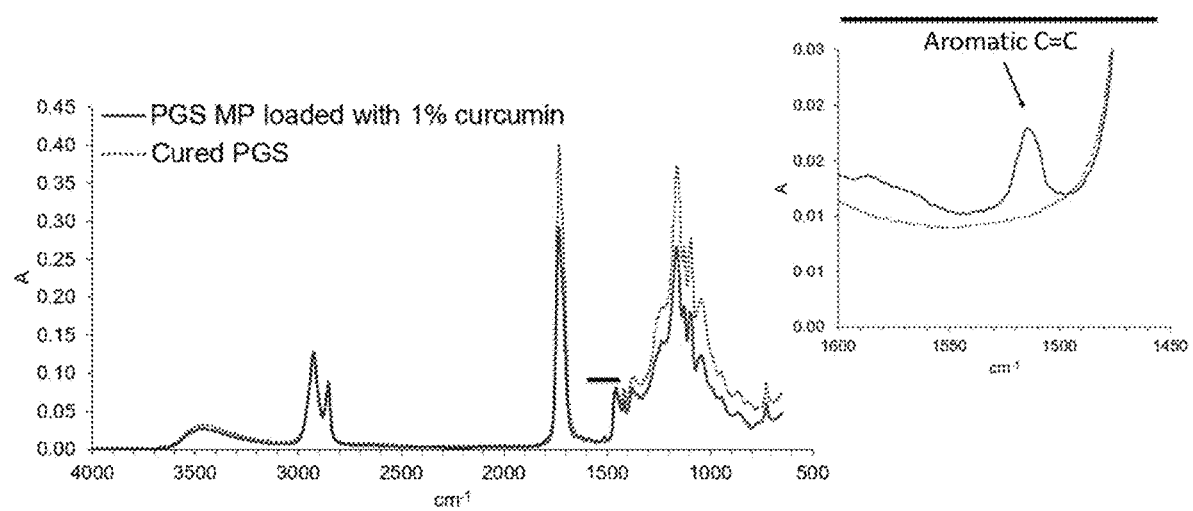
FIG. 13 is FTIR spectra of PGS microspheres loaded with curcumin by an emulsification process similar that of FIG. 6.
Figure 14:
FIG. 14 shows PGS microspheres containing curcumin.

A variation of the process described in Example 3 was prepared in which the addition of 1 wt % curcumin agent for release is captured in molten neat PGS resin that is subsequently formed into microspheres using alginate as an emulsifying agent. FIG. 13 shows FTIR spectra establishing that curcumin is present in PGS microspheres following extraction from alginate and subsequent washing steps due to aromatic C=C peak near 1500 $cm^{-1}$ only being present in curcumin molecular structure. PGS microspheres following washing are shown in FIG. 14; observation demonstrated an exhibited yellow coloration confirming the loading of curcumin that was not seen in the PGS microspheres formed without the addition of that agent.

All above-mentioned references are hereby incorporated by reference herein.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A method of forming a plurality of cured microparticles comprising:
   providing a composition comprising a poly(glycerol sebacate) resin in an uncured state and lacking a solvent; and
   forming the composition into a plurality of uncured microparticles in a phase-incompatible liquid, wherein the phase-incompatible liquid is non-reactive with the poly(glycerol sebacate), the plurality of uncured microparticles being free of a photo-induced crosslinker, and curing the plurality of uncured microparticles to form the plurality of cured microparticles, wherein the plurality of cured microparticles are free of a photo-induced crosslinker;
   wherein the poly(glycerol sebacate) resin comprises a poly(glycerol sebacate urethane) resin.

2. The method of claim 1, wherein the forming comprises combining the composition with the phase-incompatible liquid and suspending the plurality of uncured microparticles in a matrix of the phase-incompatible liquid.

3. The method of claim 2, wherein the phase-incompatible liquid is an oil.

4. The method of claim 1, wherein the forming comprises shear mixing the composition in the phase-incompatible liquid.

5. The method of claim 1, wherein the forming comprises metering the composition into a vessel containing the phase-incompatible liquid.

6. The method of claim 5, wherein the vessel is a vertical column and the metering is with a needle.

7. The method of claim 1, wherein the forming comprises sonicating the composition into the phase-incompatible liquid.

8. The method of claim 1, wherein the curing comprises conductively heating the plurality of uncured microparticles.

9. The method of claim 1, wherein the curing comprises applying microwave radiation to the plurality of uncured microparticles.

10. The method of claim 1 further comprising loading the poly(glycerol sebacate) resin with at least one controlled release agent.

11. The method of claim 1, wherein the plurality of cured microparticles are free of photoinitiators.

12. The method of claim 1, wherein the plurality of uncured microparticles consists of the poly(glycerol sebacate) resin.

13. The method of claim 1, wherein the poly(glycerol sebacate) resin further comprises a poly(glycerol sebacate acrylate) resin.

14. The method of claim 1, wherein the forming the composition into a plurality of uncured microparticles occurs without a mold and the curing the plurality of uncured microparticles to form the plurality of cured microparticles occurs without a mold.

15. The method of claim 1, wherein the poly(glycerol sebacate) resin has a weight average molecular weight in the range of from about 5,000 to about 50,000 Da.

16. A method of forming a scaffold comprising:
    providing a plurality of microparticles comprising poly(glycerol sebacate) in a three-dimensional arrangement; and
    stimulating the plurality of microparticles comprising poly(glycerol sebacate) in the three-dimensional arrangement to sinter the plurality of microparticles, thereby forming the scaffold having a plurality of pores;
    wherein the plurality of microparticles comprising poly(glycerol sebacate) in the three-dimensional arrangement further comprise a coating of poly(glycerol sebacate) resin-based glue.

17. The method of claim 16, wherein the stimulating comprises applying microwave radiation.

18. The method of claim 16, wherein the stimulating comprises convectively heating.

19. The method of claim 16, wherein the stimulating comprises curing uncured portions of the poly(glycerol sebacate) in the plurality of microparticles.

20. The method of claim 16, wherein the plurality of microparticles comprising poly(glycerol sebacate) comprises a plurality of micronized poly(glycerol sebacate) thermoset filler particles.

21. The method of claim 16, wherein the plurality of microparticles comprising poly(glycerol sebacate) further comprise at least one controlled release agent.

22. The method of claim 16, wherein the three-dimensional arrangement provides the scaffold with a spherical shape of a shell around a hollow core.

23. The method of claim 16, wherein the providing a plurality of microparticles comprising poly(glycerol sebacate) comprises providing a plurality of spherical microparticles comprising poly(glycerol sebacate).

* * * * *